(12) United States Patent
Rivas et al.

(10) Patent No.: US 10,330,642 B2
(45) Date of Patent: Jun. 25, 2019

(54) BAW SENSOR DEVICE WITH PEEL-RESISTANT WALL STRUCTURE

(71) Applicant: Qorvo US, Inc., Greensboro, NC (US)

(72) Inventors: Rio Rivas, Bend, OR (US); Vincent K. Gustafson, Chapel Hill, NC (US)

(73) Assignee: QORVO US, INC., Greensboro, NC (US)

( * ) Notice: Subject to any disclaimer, the term of this patent is extended or adjusted under 35 U.S.C. 154(b) by 146 days.

(21) Appl. No.: 15/377,378

(22) Filed: Dec. 13, 2016

(65) Prior Publication Data

US 2017/0168017 A1     Jun. 15, 2017

Related U.S. Application Data

(60) Provisional application No. 62/266,973, filed on Dec. 14, 2015.

(51) Int. Cl.
| | |
|---|---|
| *G01N 29/22* | (2006.01) |
| *G01N 29/02* | (2006.01) |
| *G01N 29/032* | (2006.01) |
| *G01N 29/036* | (2006.01) |
| *H03H 9/02* | (2006.01) |

(52) U.S. Cl.
CPC ......... *G01N 29/022* (2013.01); *G01N 29/032* (2013.01); *G01N 29/036* (2013.01); *G01N 29/222* (2013.01); *H03H 9/02007* (2013.01); *G01N 2291/014* (2013.01); *G01N 2291/015* (2013.01); *G01N 2291/0255* (2013.01); *G01N 2291/0256* (2013.01); *G01N 2291/0422* (2013.01); *G01N 2291/0423* (2013.01); *G01N 2291/0426* (2013.01)

(58) Field of Classification Search
CPC ........................... G01N 29/222; G01N 29/223
See application file for complete search history.

(56) References Cited

U.S. PATENT DOCUMENTS

| | | | |
|---|---|---|---|
| 4,640,756 A | * | 2/1987 | Wang .................. C23C 14/225 204/192.18 |
| 7,266,149 B2 | | 6/2007 | Stout et al. |
| 7,468,608 B2 | | 12/2008 | Feucht et al. |
| | | | (Continued) |

OTHER PUBLICATIONS

Qorvo US, Inc., "Summary of Sales Activity of Predecessor to Applicant Concerning Tilted C-AXIS Aluminum Nitride Products," Unpublished, Jan. 10, 2017, 1 page.

(Continued)

*Primary Examiner* — Justin N Olamit
(74) *Attorney, Agent, or Firm* — Mueting, Raasch & Gebhardt, P.A.

(57) ABSTRACT

Lateral boundaries of a fluidic passage of a fluidic device incorporating at least one BAW resonator structure are fabricated with photosensitive materials (e.g., photo definable epoxy, solder mask resist, or other photoresist), allowing for high aspect ratio, precisely dimensioned walls. Resistance to delamination and peeling between a wall structure and a base structure is enhanced by providing a wall structure that includes a thin footer portion having a width that exceeds a width of an upper wall portion extending upward from the footer portion, and/or by providing a wall structure arranged over at least one anchoring region of a base structure. Anchoring features may include recesses and/or protrusions.

21 Claims, 13 Drawing Sheets

(56) References Cited

U.S. PATENT DOCUMENTS

| | | | |
|---|---|---|---|
| 7,648,855 B2* | 1/2010 | Gillot | B81C 1/0023 257/E21.499 |
| 7,914,740 B2* | 3/2011 | Zhang | B82Y 15/00 422/50 |
| 8,409,875 B2 | 4/2013 | Johal et al. | |
| 2009/0184002 A1* | 7/2009 | Furukawa | G01N 33/5438 205/775 |
| 2015/0232912 A1* | 8/2015 | Kurioka | C12Q 1/26 435/25 |

OTHER PUBLICATIONS

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Zhou, Yan et al., "Interfacial Structures and Properties of Organic Materials for Biosensors: An Overview," Sensors, vol. 12, Nov. 6, 2012, pp. 15036-15062.

Carballo, V. M. Blanco et al., "Moisture resistance of SU-8 and KMPR as structural material for integrated gaseous detectors," 11th Annual Workshop on Semiconductor Advances for Future Electronics and Sensors, SAFE 2008, Nov. 2008, pp. 395-398.

Bowen, Ryan M., "Residual Stress in SU-8 Photoresist Films," 0305-320 Design of Experiments Project, Department of Microsystems Engineering, Rochester Institute of Technology, Mar. 2012, 7 pages.

Wangler, N. et al., "High-resolution permanent photoresist laminate TMMF for sealed microfluidic structures in biological applications," Journal of Micromechanics and Microengineering, vol. 21, Aug. 4, 2011, IOP Publishing, 9 pages.

Carballo et al., "Moisture Resistance of SU-8 and KMPR as Structural Material for Integrated Gaseous Detectors," 11th Annual Workshop on Semiconductor Advances for Future Electronics and Sensors, Veldhoven, The Netherlands, Nov. 27-28, 2008, *SAFE 2008*; pp. 395-398.

Wouters, et al., "Accurate Measurement of the Steady-State Swelling Behavior of SU-8 Negative Photo Resist," Sep. 2009, *Procedia Chemistry*, 1(1):60-63.

* cited by examiner ial content on this page:

BAW SENSOR DEVICE WITH PEEL-RESISTANT WALL STRUCTURE

STATEMENT OF RELATED APPLICATIONS

This application claims the benefit of provisional patent application Ser. No. 62/266,973, filed Dec. 14, 2015, the disclosure of which is hereby incorporated herein by reference in its entirety.

TECHNICAL FIELD

The present disclosure relates to fluidic devices incorporating acoustic resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, amplitude-magnitude, or phase characteristics of the acoustic wave device, and can be correlated to a physical quantity being measured.

In the case of a piezoelectric crystal resonator, an acoustic wave may embody either a bulk acoustic wave (BAW) propagating through the interior of a piezoelectric material, or a surface acoustic wave (SAW) propagating on the surface of the piezoelectric material. SAW devices involve transduction of acoustic waves (commonly including two-dimensional Rayleigh waves) utilizing interdigital transducers along the surface of a piezoelectric material, with the waves being confined to a penetration depth of about one wavelength. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes, as the particle vibration, or polarization, is neither purely parallel nor purely perpendicular to the propagation direction. The propagation characteristics of the respective modes depend on the material properties and propagation direction respective to the c-axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electro-mechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Sensing devices incorporating BAW resonator structures and intended for use with fluids may define fluidic passages to direct fluid over an active region. Structures defining fluidic passages may incorporate wall structures and cover structures. The small dimensions associated with sensing regions may render it challenging to fabricate wall structures that (i) define fluidic passages appropriately aligned with resonator active regions without occlusion and (ii) resist peeling from an underlying substrate. For example, when inter-layer adhesives are used to assemble precut layers (e.g., including wall layers) of a multi-layer sensing device, it may be difficult to provide adhesive in a sufficient amount to promote proper adhesion without providing excess adhesive that may flow into a fluidic passage. Alternatively, if curable materials are used to define wall structures of a sensing device, it may be challenging to promote persistent bonding between the wall structures and a substrate (and thereby preventing peeling of the wall structures), particularly when wall structures having elevated wall height/width aspect ratios are provided, and when wall structures are exposed to fluids and/or humid operating environments.

Accordingly, there is a need for devices incorporating bulk acoustic wave resonator structures suitable for operation in the presence of liquid for biosensing or biochemical sensing applications that overcome limitations associated with conventional devices.

SUMMARY

The present disclosure provides fluidic devices incorporating BAW resonator structures with wall structures that resist peeling (e.g., delamination) from a base structure. One or more wall structures define lateral boundaries of a fluidic passage arranged to receive a fluid and containing an active region of a BAW resonator structure, wherein the wall structures may be advantageously produced with photoresist (e.g., SU-8) or epoxy materials. In certain embodiments, peel resistance is enhanced by providing a wall structure that includes a footer portion having a width that exceeds a width of an upper wall portion extending upward from the footer portion. In certain embodiments, peel resistance is enhanced by providing a wall structure arranged over at least one anchoring region of a base structure, wherein the at least one anchoring region includes at least one anchoring feature, and the at least one anchoring feature includes at least one recess and/or at least one protrusion (optionally, multiple recesses and/or multiple protrusions). In certain embodiments, peel resistance may be further enhanced by providing a wall structure including a footer portion having a width that exceeds a width of an upper wall portion, with the footer portion being arranged over at least one anchoring region of a base structure. Methods for fabricating a fluidic device as disclosed herein, as well as methods for biological or chemical sensing using such a fluidic device, are further provided.

In one aspect, the disclosure relates to a fluidic device comprising a base structure and a wall structure that includes a footer portion and an upper wall portion. In particular, the base structure comprises: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region. The wall structure is arranged over at least a portion of the base structure and defines lateral boundaries of a fluidic passage arranged to receive a fluid and containing the active region, wherein: the wall structure comprises a footer portion and an upper wall portion that protrudes upward from the footer portion; the footer portion is arranged between the upper wall portion and the base structure; and the footer portion comprises a width that exceeds a width of the upper wall portion.

In certain embodiments, the fluidic device further includes a cover structure arranged over the wall structure and defining an upper boundary of the fluidic passage.

In certain embodiments, the wall structure and the cover structure are embodied in a monolithic body structure. In certain embodiments, the wall structure comprises at least one of a photosensitive material, photoresist, or epoxy.

In certain embodiments, the fluidic device further includes at least one functionalization material arranged over at least a portion of the active region. In certain embodiments, the fluidic device further includes a self-assembled monolayer arranged between the at least one functionalization material and the top side electrode. In certain embodiments, the fluidic device further includes an interface layer arranged between the self-assembled monolayer and the top side electrode. In certain embodiments, the fluidic device further includes a hermeticity layer arranged between the interface layer and the top side electrode.

In certain embodiments, the piezoelectric material comprises a c-axis having an orientation distribution that is predominantly non-parallel to normal of a face of the substrate.

In another aspect, the disclosure relates to a fluidic device comprising a base structure including at least one anchoring feature (e.g., at least one recess and/or at least one protrusion), and a wall structure arranged over the at least one anchoring region and defining lateral boundaries of a fluidic passage arranged to receive a fluid. In particular, the base structure comprises: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region, and wherein a portion of the base structure comprises at least one anchoring region including at least one anchoring feature, and the at least one anchoring feature comprises at least one of: (i) at least one recess or (ii) at least one protrusion. The wall structure is arranged over the at least one anchoring region and defines lateral boundaries of a fluidic passage arranged to receive a fluid and containing the active region.

In certain embodiments, the at least one anchoring feature comprises a vertical dimension of least about 1 micron. In certain embodiments, the at least one recess comprises a plurality of recesses, and the at least one protrusion comprises a plurality of protrusions In certain embodiments, the fluidic device further comprises a cover structure arranged over the wall structure and defining an upper boundary of the fluidic passage. In certain embodiments, the wall structure and the cover structure are embodied in a monolithic body structure. In certain embodiments, the wall structure comprises at least one of a photosensitive material, photoresist, or epoxy In certain embodiments, the fluidic device further includes at least one functionalization material arranged over at least a portion of the active region. In certain embodiments, the fluidic device further includes a self-assembled monolayer arranged between the at least one functionalization material and the top side electrode. In certain embodiments, the fluidic device further includes an interface layer arranged between the self-assembled monolayer and the top side electrode. In certain embodiments, the fluidic device further includes a hermeticity layer arranged between the interface layer and the top side electrode.

In another aspect, a method for biological or chemical sensing comprises: supplying a fluid containing an analyte into the fluidic passage of a fluidic device disclosed herein, wherein said supplying is configured to cause at least some of the analyte to bind to the at least one functionalization material; inducing a bulk acoustic wave in the active region; and sensing a change in at least one of an amplitude-magnitude property, a frequency property, or a phase property of the at least one bulk acoustic wave resonator structure to indicate at least one of presence or quantity of target species bound to the at least one functionalization material.

In another aspect, any one or more aspects or features of one or more embodiments may be combined with aspects or features of one or more other embodiments for additional advantage, unless indicated to the contrary herein Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

Figure 1:
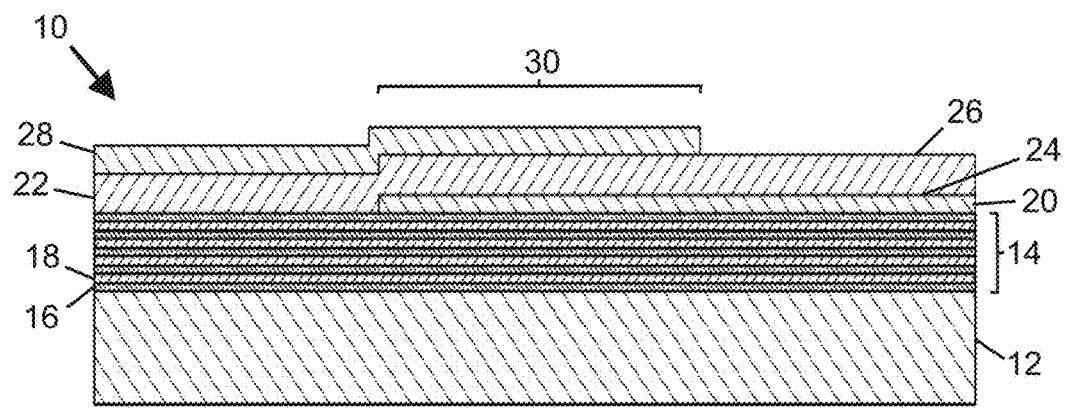
FIG. 1 is a schematic cross-sectional view of a portion of a bulk acoustic wave (BAW) MEMS resonator device usable for fabricating fluidic devices according to embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure provides fluidic devices incorporating BAW resonator structures with wall structures that resist peeling (e.g., delamination) from a base structure. One or more wall structures define lateral boundaries of a fluidic passage arranged to receive a fluid and containing an active region of a BAW resonator structure, wherein the wall structures may be advantageously produced with photoresist (e.g., SU-8) or epoxy materials. In certain embodiments, peel resistance is enhanced by providing a wall structure that includes a footer portion having a width that exceeds a width of an upper wall portion extending upward from the footer portion. In certain embodiments, peel resistance is enhanced by providing a wall structure arranged over at least one anchoring region of a base structure, wherein the at least one anchoring region includes at least one anchoring feature, and the at least one anchoring feature includes at least one recess and/or at least one protrusion (optionally, multiple recesses and/or multiple protrusions). In certain embodiments, peel resistance may be further enhanced by providing a wall structure including a footer portion having a width that exceeds a width of an upper wall portion, with the footer portion being arranged over at least one anchoring region of a base structure. Methods for fabricating a fluidic device as disclosed herein, as well as methods for biological or chemical sensing using such a fluidic device, are further provided.

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode. Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein.

Before describing fluidic devices incorporating BAW resonator structures and including wall structures that resist peeling (e.g., delamination) from a base structure, exemplary bulk acoustic wave MEMS resonator devices, associated layers useful for providing biochemical sensing utility, and fluidic devices incorporating MEMS resonator devices will be introduced.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with the active region of the BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

FIG. 1 is a schematic cross-sectional view of a portion of a bulk acoustic wave (BAW) MEMS resonator device 10 useable for fabricating fluidic devices according to at least certain embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28. In certain embodiments, the piezoelectric material 22 comprises a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate 12.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or a functionalization material (which may include specific binding material or non-specific binding material).

Figure 2:
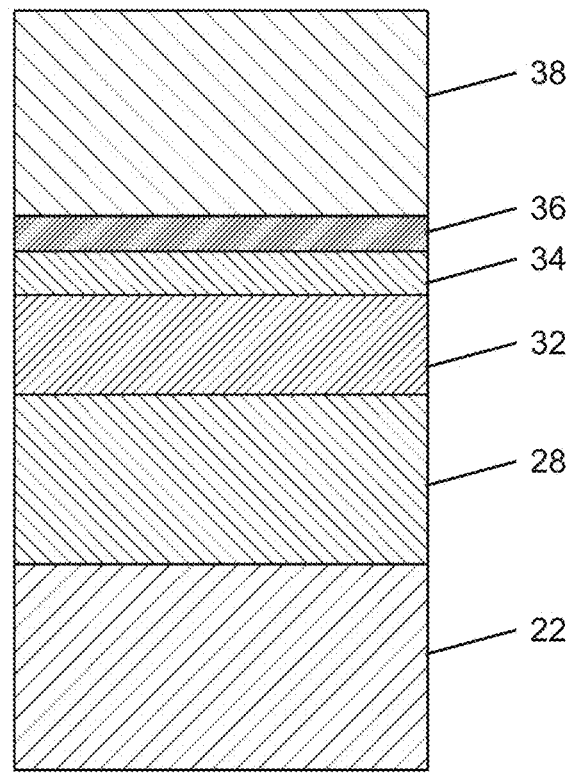
FIG. 2 is a schematic cross-sectional view of an upper portion of a BAW MEMS resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of the interface layer 34 to prevent localized attachment of one or more subsequently deposited layers, or (if applied over selected regions of the SAM 36 or functionalization material 38) to prevent analyte capture in regions not overlying the active region 30 of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide [$Al_2O_3$] or silicon nitride [SiN]. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a backbone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithographic masking and selective etching for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active regions of a multi-resonator structure (i.e., one or more resonator structures including multiple active regions), optionally in combination with one or more active regions that are devoid of specific binding materials to serve as comparison (or "reference") regions. In certain embodiments, a functionalization (e.g., bio-functionalization) material may provide non-specific binding utility.

Certain embodiments are directed to a fluidic device including multiple bulk acoustic wave (BAW) MEMS resonator structures as disclosed herein and including a fluidic passage (e.g., a channel, a chamber, or the like) arranged to conduct a liquid to contact at least one functionalization (e.g., specific binding) material arranged over at least one active region of the BAW MEMS resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of the microfluidic passage; in other embodiments, functionalization material may be applied over an active region of a bulk acoustic wave resonator structure following formation of the microfluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 3:
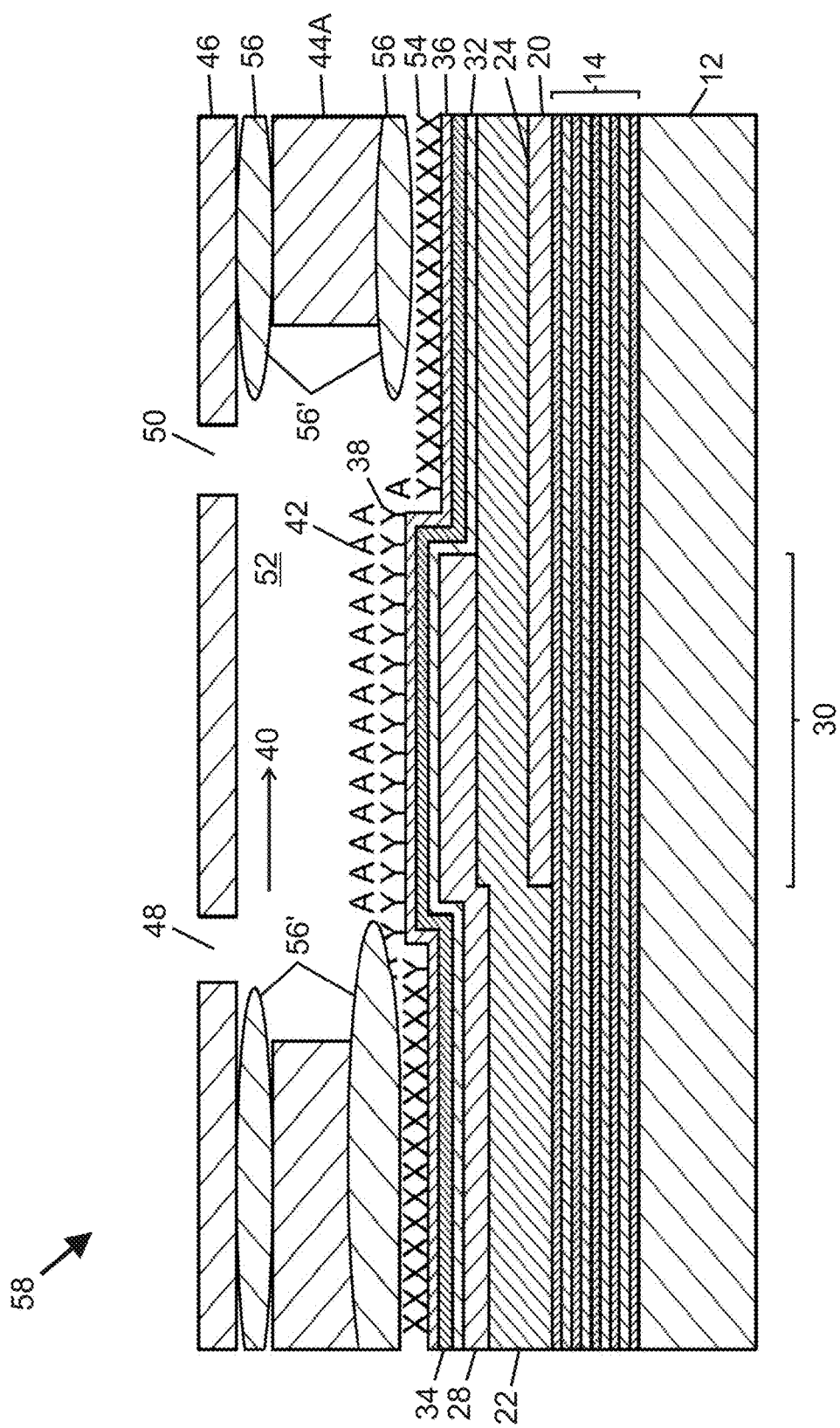
FIG. 3 is a side cross-sectional schematic view of a portion of a fluidic device (e.g., a biochemical sensor device) fabricated with laser-cut laminate layers including a fluidic passage bounded from below by a base structure including a BAW resonator structure, bounded laterally by a wall layer, and bounded from above by a cover or cap layer, showing incursion of excess inter-layer adhesive into the fluidic passage and serving as a first comparison device intended to provide context for subsequently described embodiments of the disclosure.

FIG. 3 is a side cross-sectional schematic view of a portion of a fluidic device 58 (e.g., a biochemical sensor device) fabricated with laser-cut laminate layers including a fluidic passage 52 bounded from below by a base structure including a BAW resonator structure, bounded laterally by a wall structure embodied in a pre-cut (e.g., laser-cut) wall layer 44A, and bounded from above by a cover or cap layer 46, wherein the fluidic device 58 serves as a first comparison device to provide context for subsequently described embodiments of the disclosure.

The fluidic device 58 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the wall layer 44A are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Walls of the wall layer 44A are laterally displaced from the active region 30 and extend upward from the blocking material 54 to define lateral boundaries of the fluidic passage 52 containing the active region 30. The cover or cap layer 46 defines fluidic inlet and outlet ports 48, 50 (suitable for admitting a fluid volume 40 such as an analyte-containing sample) and is further provided to provide an upper boundary for the fluidic passage 52. The cover or cap layer 46 may be formed by defining fluidic inlet and outlet ports 48, 50 (e.g., via laser cutting or water jet cutting) in a layer of an appropriate material (e.g., a substantially inert polymer, glass, silicon, ceramic, or the like), and adhering the cover or cap layer 46 to top surfaces of the wall layer 44A.

The wall layer 44A is formed of a laser-cut "stencil" layer of thin polymeric material and/or laminate material, coated with adhesive material 56 to promote adhesion to the underlying blocking material 54 and to the overlying cover or cap layer 46. For example, the wall layer 44A and the adhesive material 56 may include adhesive tape. One challenge associated with devices fabricated with laser cut laminates is that excess adhesive material 56 present on one or more surfaces of the wall layer 44A is prone to "squish"—i.e., to be compressively ejected from between layers. Such effect is shown in FIG. 3, in which ejected portions 56' of adhesive material 56 extend into the fluidic passage 52, and undesirably cover a portion of the functionalization material 38 proximate to the active region 30. In extreme cases, ejected portions 56' of adhesive material 56 may interfere with operation of the fluidic device 58. Another challenge with laser cut laminates is difficulty in aligning the wall layer 44A and cover or cap layer 46 to one another and to the underlying base structure. The imprecise alignment results both from poor tolerance of the laser-cut layers and the manual alignment process, and tends to lead to architectures with larger than desired feature sizes.

During intended use of the fluidic device 58, a fluid volume 40 may be supplied through the fluidic inlet port 48 into the fluidic passage 52 over the active region 30 and then flow through the fluidic outlet port 50 to exit the fluidic passage 52. Due to the laminar nature of the fluid flow within the fluidic passage 52, the fluid volume 40 may be modeled and behave as a "stack" of horizontal fluid layers. An analyte 42 contained in one or more lower layers of the fluid volume 40 may bind with functionalization material 38 arranged over the active region 30. Assuming that sufficient analyte is present to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38.

The above-described challenges associated with fluidic devices incorporating BAW resonator structures (e.g., biochemical sensor devices) fabricated with stencil-based wall structures have led the Applicant to utilize photosensitive materials for forming wall layer structures. An example of a suitable photosensitive material is an epoxy material such SU-8, which can form precisely dimensioned structures with high height/width aspect ratios, and has excellent biomedical compatibility. In use, a photosensitive material may be applied over a surface, a photomask may be placed thereover, and energy such as ultraviolet emissions or proton beams may be transmitted through openings in the photomask to selectively cure the photosensitive material to form microstructures. Beyond SU-8, other suitable materials for forming photo-defined wall layer structures include TMMF epoxy (e.g., a high resolution permanent dry film photoresist composed of 5% antimony compound and 95% novolak-type epoxy resin) as well as other photoresist and solder mask materials.

Figure 4A:
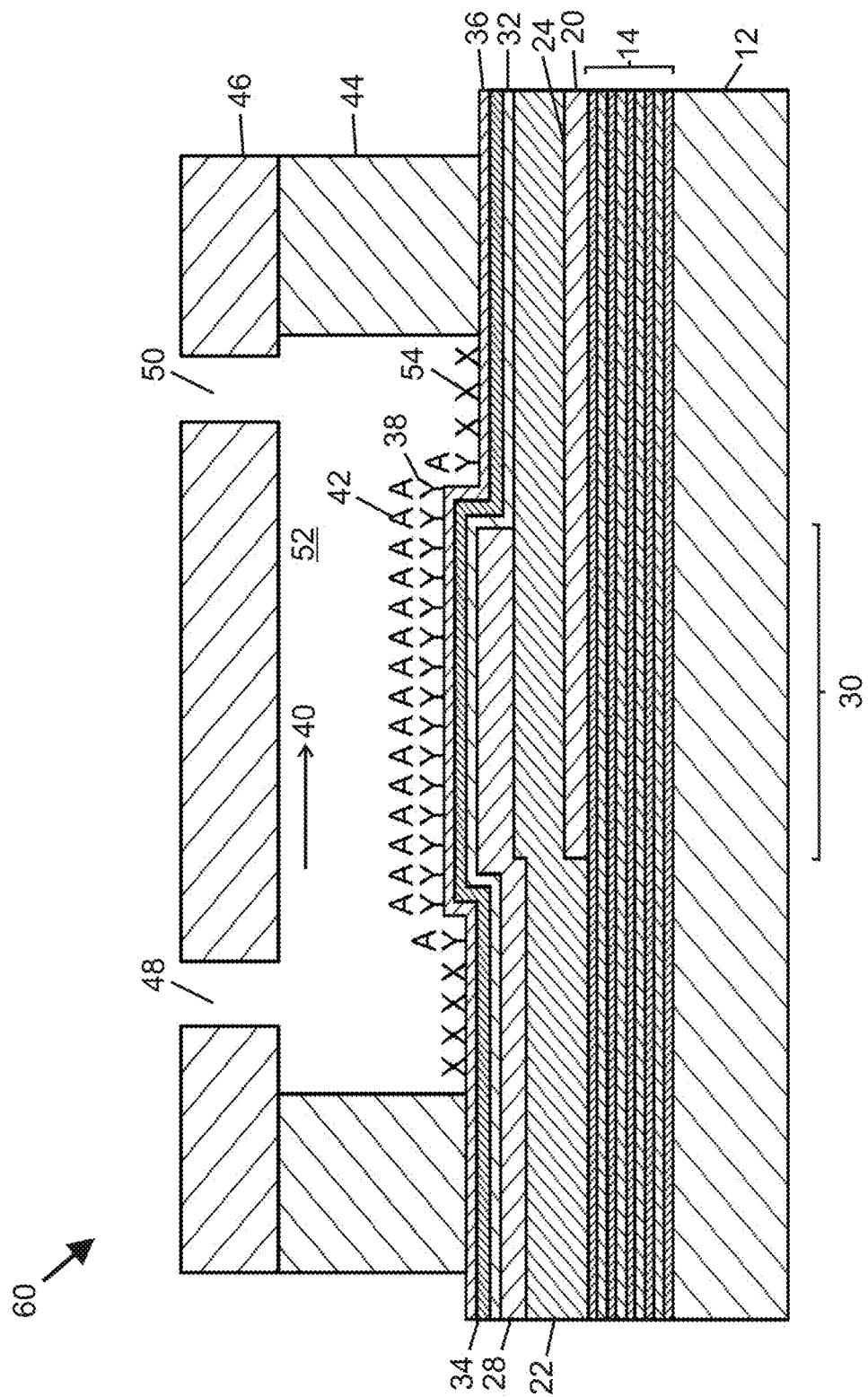
FIG. 4A is a schematic cross-sectional view of a portion of a fluidic device (e.g., a biochemical sensor device) including a fluidic passage bounded from below by a base structure including a BAW resonator structure, bounded laterally by a wall structure fabricated of photosensitive (e.g., epoxy or photoresist) materials, and bounded from above by a cover or cap layer, serving as a second comparison device intended to provide context for subsequently described embodiments of the disclosure.

FIG. 4A is a schematic cross-sectional view of a portion of a fluidic device 60 (e.g., a biochemical sensor device) including a fluidic passage 52 bounded from below by a base structure including a BAW resonator structure, bounded laterally by a wall structure 44 fabricated of photosensitive (e.g., epoxy or photoresist) materials, and bounded from above by a cover or cap layer 46. For example, the wall structure 44 may be fabricated of SU-8 epoxy. The fluidic device 60 serves as a second comparison device intended to provide context for subsequently described embodiments of the disclosure. As compared to the fluidic device 58 of FIG. 3, the fluidic device 60 of FIG. 4A lacks adhesive material 56 between the wall structure 44 and the adjacent structures, such that the fluidic device 60 does not exhibit any compressive ejection or "squish" of adhesive between layers.

With continued reference to FIG. 4A, the fluidic device 60 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the wall structure 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Walls of the wall structure 44 are laterally displaced from the active region 30 and extend upward from the SAM 36 to define lateral boundaries of the fluidic passage 52 containing the active region 30. The cover or cap layer 46 defines fluidic inlet and outlet ports 48, 50 (suitable for admitting a fluid volume 40 such as an analyte-containing sample) and is further provided to provide an upper boundary for the fluidic passage 52. The cover or cap layer 46 may be fabricated of a photosensitive material, or may be fabricated of other materials such as machined glass or silicon, or composite material. Operation of the fluidic device 60 is substantially similar to the operation of the fluidic device 58 described in connection with FIG. 3.

While photosensitive materials such as SU-8 can provide structures with precisely defined features, stress and adhesion embody challenges when fabricating wall structures from such materials. For example, SU-8 has a high degree of stress relative to an underlying substrate. Intrinsic stress is generated during crosslinking, and extrinsic stress is imposed due to a coefficient of thermal expansion (CTE) mismatch between SU-8 and the underlying substrate. These stresses and the thickness of a wall structure fabricated with SU-8 apply a moment (force times distance (exerted over the height of a wall structure), resulting in application of torque) on a joint between the wall structure and the underlying base structure (e.g., including a substrate or layers deposited over a substrate). This moment can tend to delaminate a wall structure from an underlying base structure, thereby opening the joint therebetween, and tending to compromise structural and/or sealing integrity of a fluidic device incorporating a BAW resonator structure.

Figure 4B:
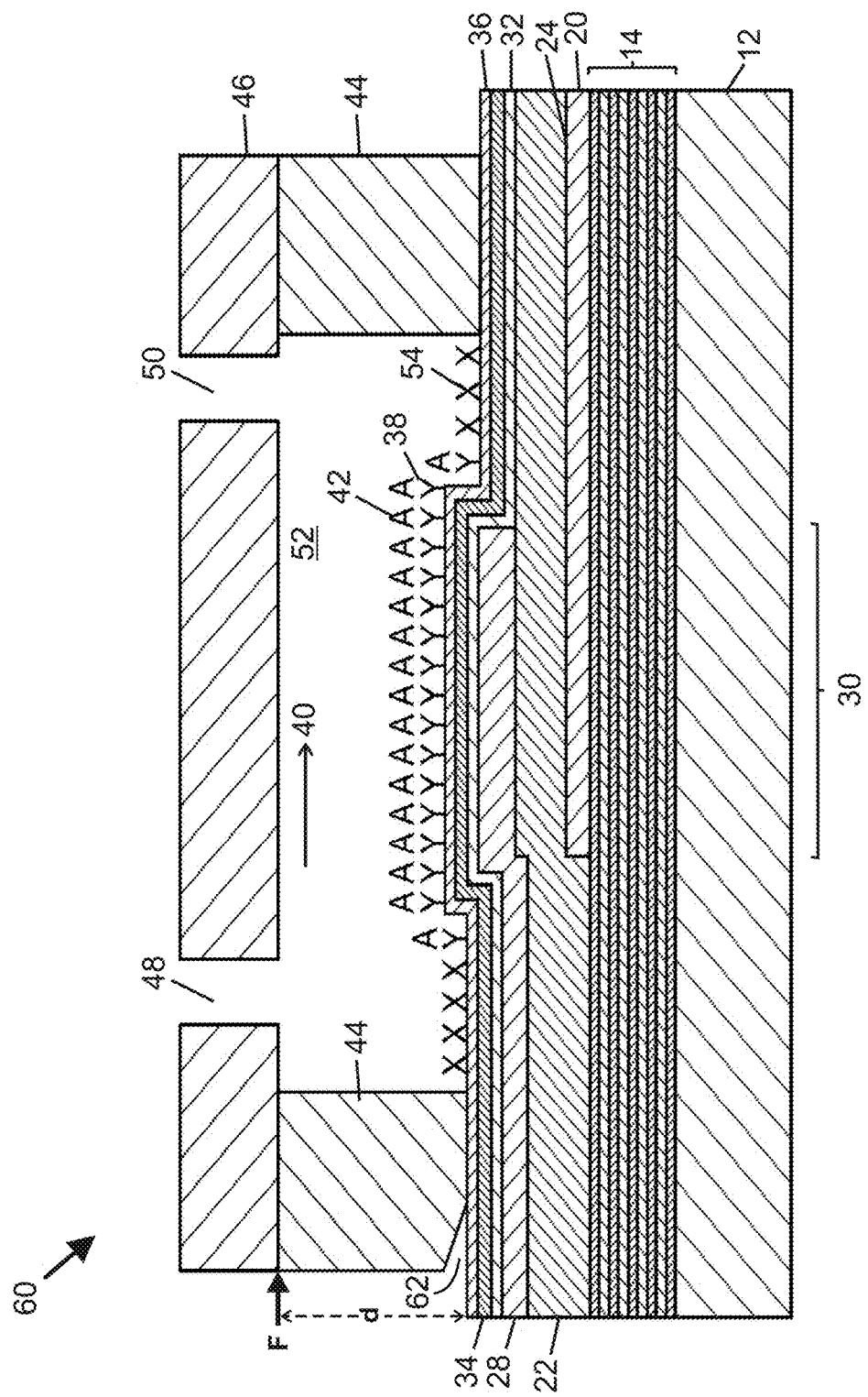
FIG. 4B is a schematic cross-sectional view of the fluidic device portion of FIG. 4A, showing a delamination crack between a left side wall structure and the base structure.

Delamination between the wall structure 44 and the SAM 36 of a base structure incorporating the BAW resonator structure of the fluidic device 60 is shown in FIG. 4B. FIG. 4B is a schematic cross-sectional view of the fluidic device portion of FIG. 4A, showing a delamination crack 62 between a left side wall structure 44 and the SAM 36 upon application of a moment caused by intrinsic and extrinsic stress of the wall structure 44, with the moment equaling the product of the force F and the distance d. Additionally, SU-8 can absorb liquid, and liquid absorption can change the stress levels. Thus, delamination (e.g., opening or "unzipping" of a bond joint) may be hastened when the wall structure 44 is exposed to fluids and/or humid operating environments.

Figure 5:
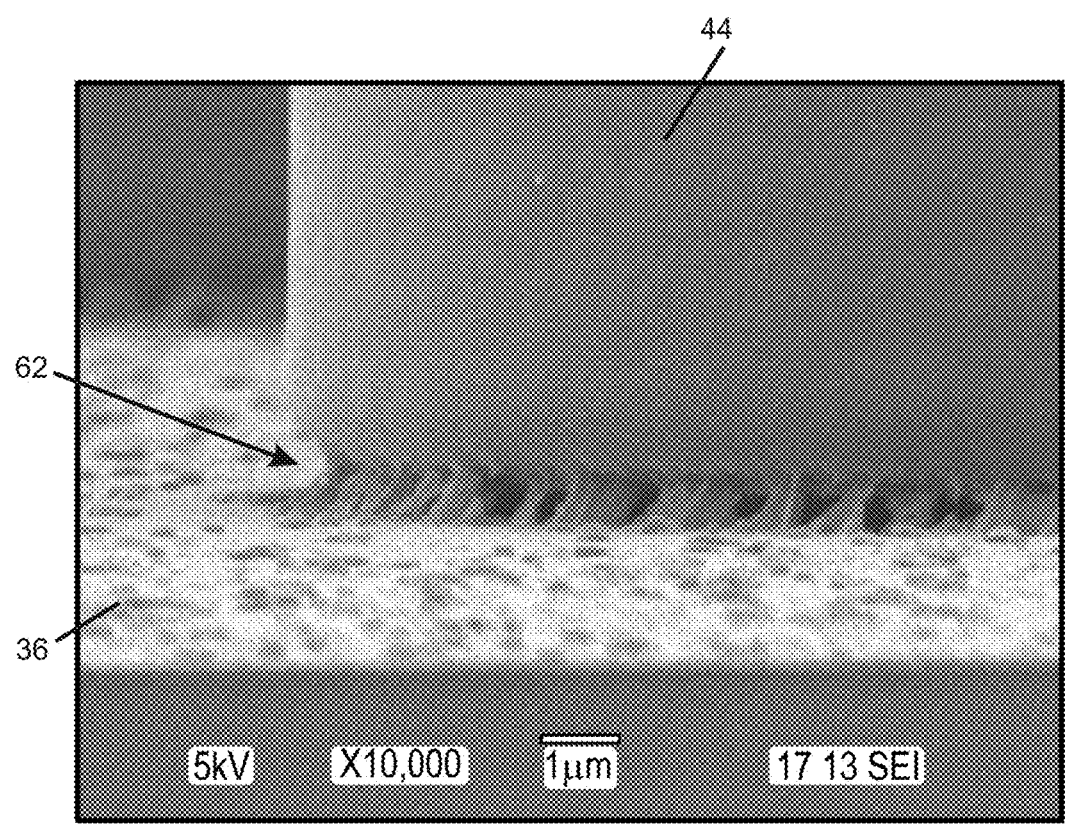
FIG. 5 is a scanning electron microscope (10,000 times magnification) of a base portion of an epoxy- or resist-based wall structure proximate to a base structure, showing a delamination crack between the wall structure and the base structure after exposure to a humidity source.

FIG. 5 is a scanning electron microscope (10,000 times magnification) of a base portion of a photosensitive material (e.g., epoxy- or resist-based) wall structure 44 proximate to a base structure (e.g., including a SAM 36 along an upper surface thereof), showing a delamination crack 62 between the wall structure 44 and the base structure after exposure to a humidity source.

In certain embodiments, a wall structure (e.g., fabricated of photosensitive material such as SU-8 epoxy) may include a footer portion and an upper wall portion extending upward therefrom, with the footer portion having a width that exceeds a width of the upper wall portion. A lateral edge of the footer portion is preferably non-coincident with, and outwardly displaced relative to, a lateral edge of the upper wall portion. Additionally, a footer portion is preferably thinner than an upper wall portion of a wall structure. In one exemplary embodiment, a footer portion may include a thickness in a range of from 1 to 20 microns, and an upper wall portion may include a thickness in a range of from 10 to 100 microns. In certain embodiments, an upper wall portion may be from 5 to 15 times thicker than a footer portion of a wall structure. Providing a wider footer portion underlying the upper wall portion tends to reduce the risk of delamination or peeling at an interface between the wall structure and an underlying base structure, since any moment applied by the upper wall portion is preferably not transmitted to a lateral edge of the footer portion. Additionally, an interface between a footer portion and an upper wall portion may characterized by a high degree of adhesion, particularly if such portions comprise the same material. Moreover, fabricating the wall structure in multiple parts may reduce intrinsic stress generated during manufacture. The footer portion may also serve as a stress relief layer. The net result is to increase robustness of adhesion between a wall structure and an underlying base structure, therefore reducing the risk of delamination and peeling between such structures.

Figure 6A:
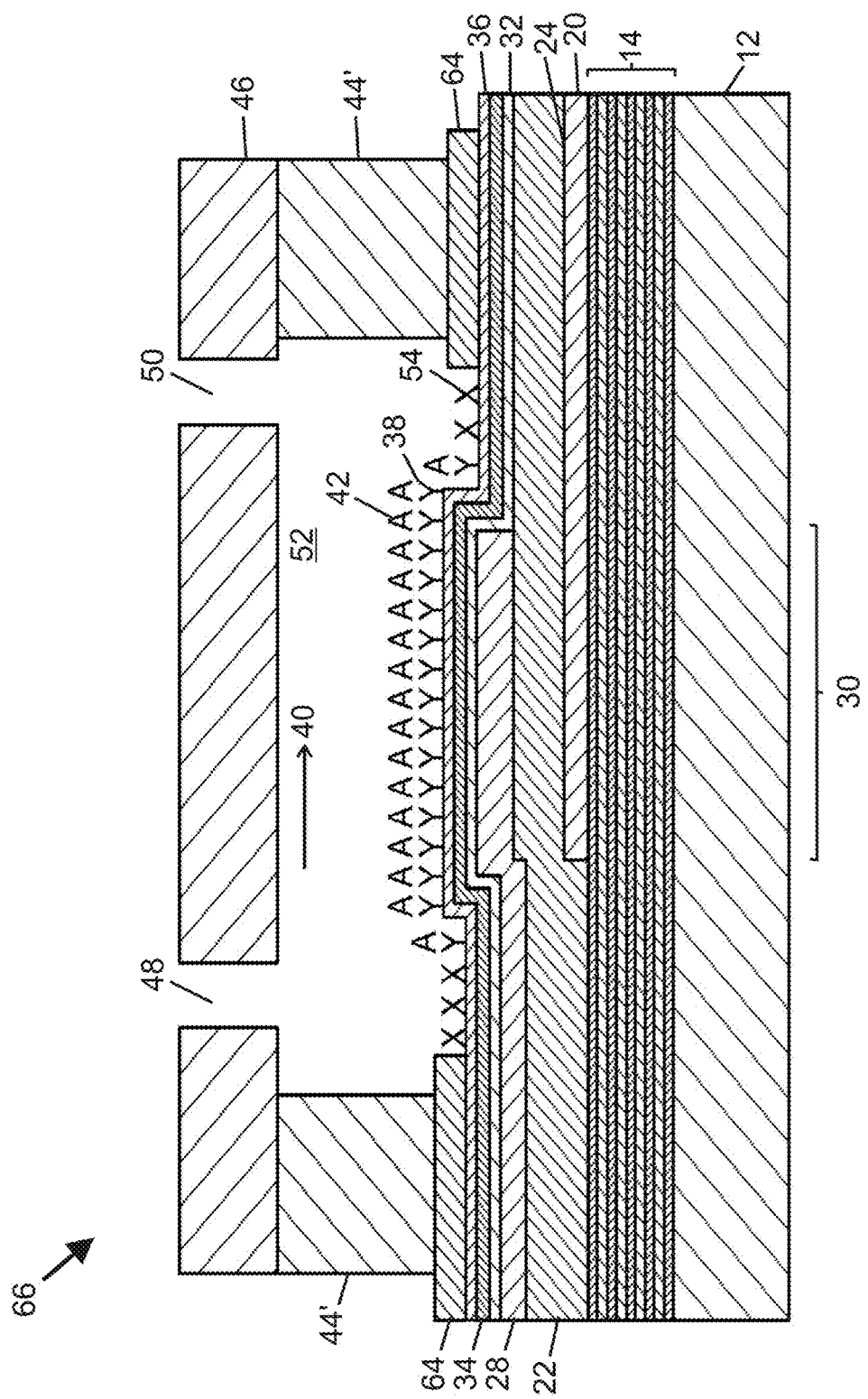
FIG. 6A is a schematic cross-sectional view of a portion of a fluidic device (e.g., a biochemical sensor device) including a fluidic passage bounded from below by a base structure including a BAW resonator structure, bounded from above by a cover or cap layer, and bounded laterally by a wall structure fabricated with photo-defined epoxy or resist materials, with the wall structure including a footer portion having a width that exceeds a width of an upper wall portion, according to one embodiment.
Figure 6B:
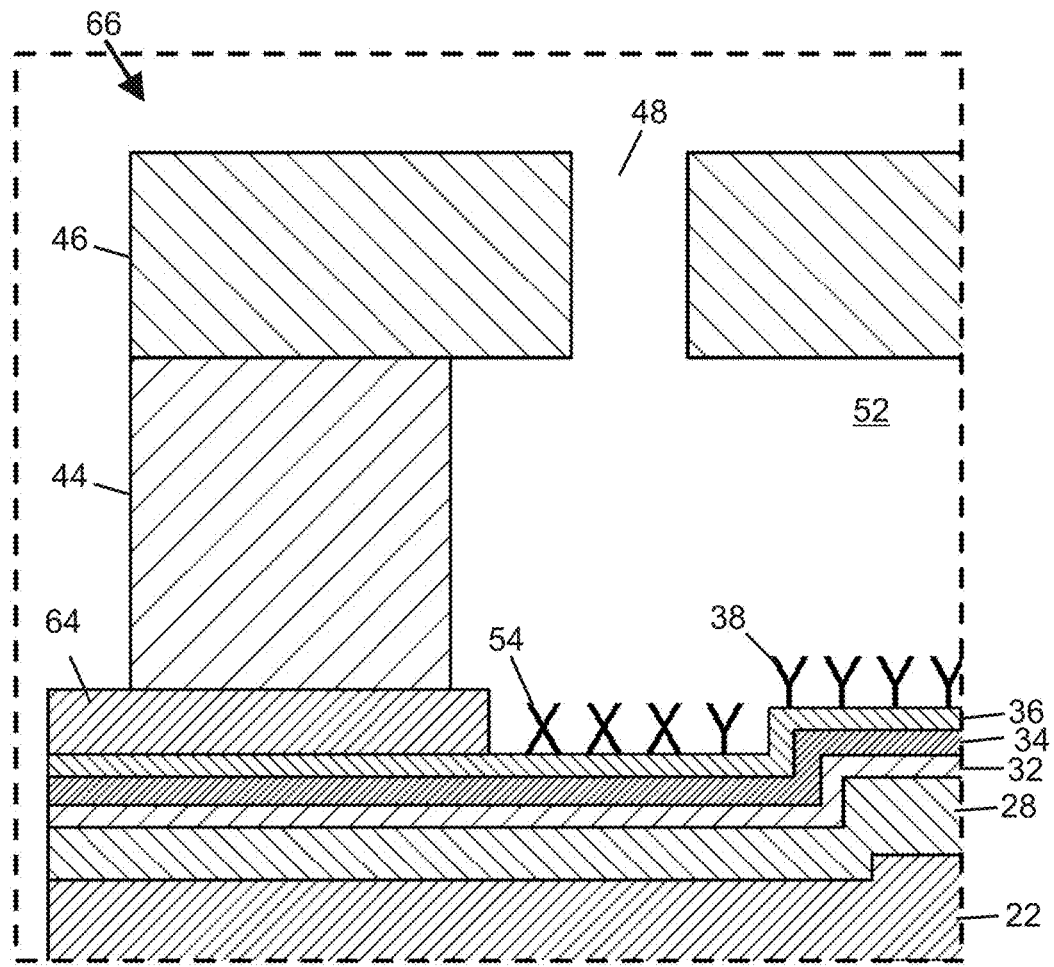
FIG. 6B is a magnified cross-sectional schematic view of an upper portion of the portion of the fluidic device shown in FIG. 6A.

FIG. 6A is a schematic cross-sectional view of a portion of a fluidic device 66 (e.g., a biochemical sensor device) including a fluidic passage 52 bounded from below by a base structure including a BAW resonator structure, bounded from above by a cover or cap layer 46, and bounded laterally by a wall structure fabricated of photosensitive (e.g., photo-defined epoxy or resist) materials including a wider footer portion 64 and a narrower upper wall portion 44' both fabricated with photo-defined epoxy or resist materials, according to one embodiment. The fluidic device 66 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the footer portion 64 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Wall structures consisting of a wider footer portion 64 and a narrower upper wall portion 44' are laterally displaced from the active region 30 and extend upward from the SAM 36 to define lateral boundaries of the fluidic passage 52 containing the active region 30. The cover or cap layer 46 defines fluidic inlet and outlet ports 48, 50 (suitable for admitting a fluid volume 40 such as an analyte-containing sample) and is further provided to provide an upper boundary for the fluidic passage 52. FIG. 6B is a magnified cross-sectional schematic view of an upper portion of the fluidic device 66 shown in FIG. 6A. Operation of the fluidic device 66 is similar to the operation of the fluidic device 58 described in connection with FIG. 3.

In certain embodiments, peel resistance is enhanced by providing a wall structure (e.g., fabricated of photosensitive material such as SU-8 epoxy) arranged over at least one anchoring region of a base structure, wherein the at least one anchoring region includes at least one anchoring feature, and the at least one anchoring feature includes at least one recess and/or at least one protrusion (optionally, multiple recesses and/or multiple protrusions). Presence of one or more anchoring regions promotes stronger adhesion between a wall structure and an underlying base structure (whether or not used in combination with a wall structure embodied in a footer portion and an upper wall portion as described above). In certain embodiments, multiple protrusions and/or recesses of an anchoring region may be embodied in a textured surface having a repeating textural pattern. In certain embodiments, each anchoring feature comprises a vertical dimension of least about 1 micron. Protrusions and/or recesses of an anchoring region may be formed in or on a base structure by methods such as selective etching (e.g., preceded by photolithographic patterning), three-dimensional printing, laser micromachining, selective deposition, and the like. More generally, protrusions and/or recesses of an anchoring region may be formed by a subtractive material removal process (e.g., etching, laser micromachining, etc.), and/or an additive manufacturing process (e.g., involving deposition of materials such as SU-8, photoresist, Parylene, epoxy, polymers, etc.). In certain embodiments, protrusions and/or recesses of an anchoring region may be defined prior to application of one or more of: a hermeticity layer, an interface layer, a self-assembled monolayer, a blocking material, or any other desired layer.

Figure 7:
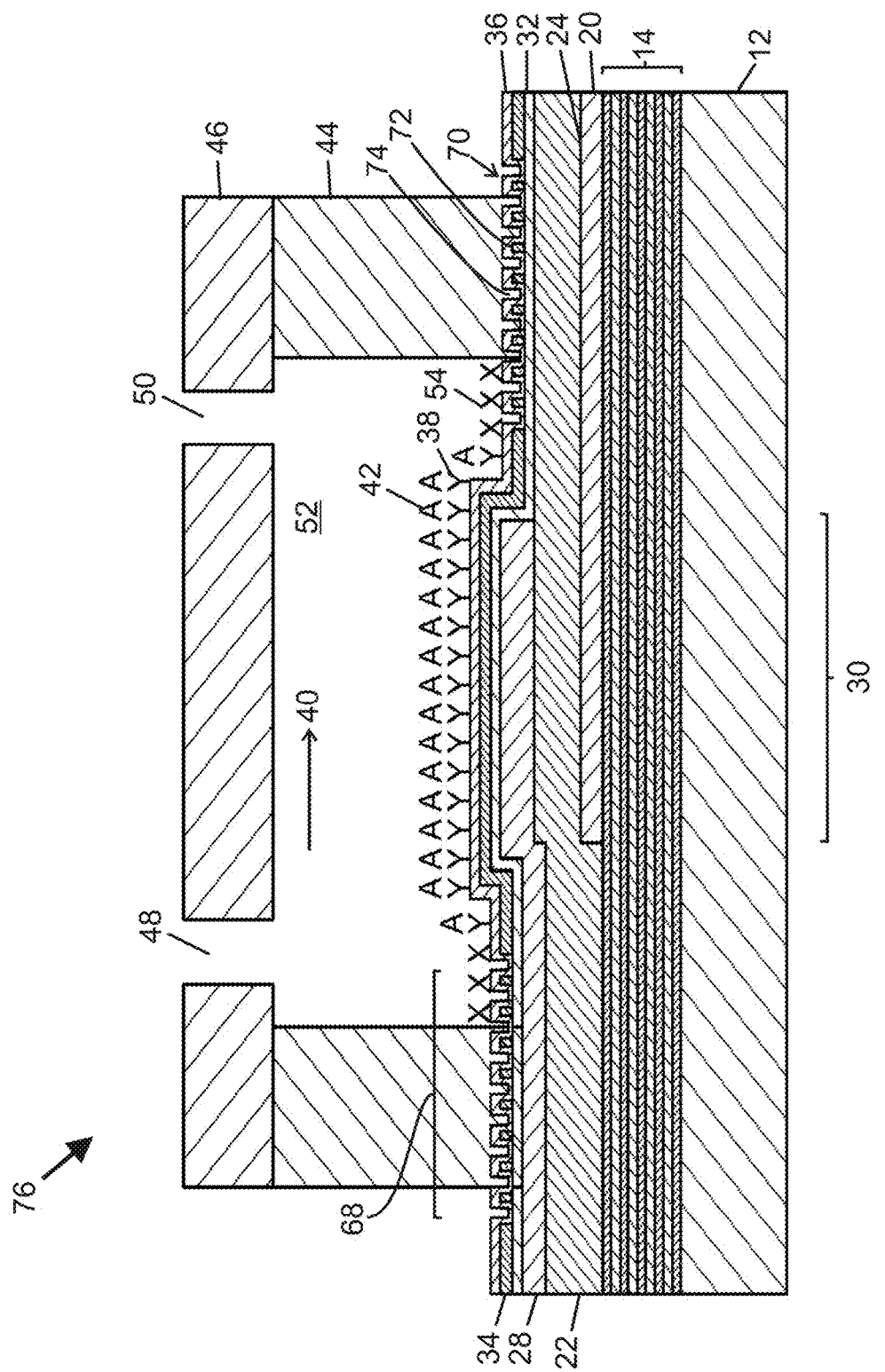
FIG. 7 is a schematic cross-sectional view of a portion of a fluidic device (e.g., a biochemical sensor device) including a fluidic passage bounded from below by a base structure including a BAW resonator structure, bounded from above by a cover or cap layer, and bounded laterally by a wall structure fabricated from photo-defined epoxy or resist materials, with the wall structure overlying anchoring regions including recesses and/or protrusions defined in or on the base structure, according to one embodiment.

FIG. 7 is a schematic cross-sectional view of a portion of a fluidic device 76 (e.g., a biochemical sensor device) including a fluidic passage 52 bounded from below by a base structure including a BAW resonator structure, bounded from above by a cover or cap layer 46, and bounded laterally by a wall structure 44 fabricated with photo-defined epoxy or resist materials, with the wall structure 44 overlying anchoring regions 68 each including recesses 74 and/or protrusions 70 defined in or on the base structure, according to one embodiment. In certain embodiments, each protrusion 70 includes an upwardly extending segment 72 of an underlying layer (e.g., an interface layer 34) that is overlaid with a substantially continuous self-assembled monolayer 36.

The fluidic device 76 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the wall structure 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Anchoring regions 68 include protrusions 70 and recesses 74, and are laterally displaced from (thereby being non-coincident with) the active region 30. The wall structure 44 extends upward from the anchoring regions 68 to define lateral boundaries of the fluidic passage 52 containing the active region 30. The cover or cap layer 46 defines fluidic inlet and outlet ports 48, 50 (suitable for admitting a fluid volume 40 such as an analyte-containing sample) and is further provided to provide an upper boundary for the fluidic passage 52. Operation of the fluidic device 76 is substantially similar to the operation of the fluidic device 58 described in connection with FIG. 3.

Figure 8A:
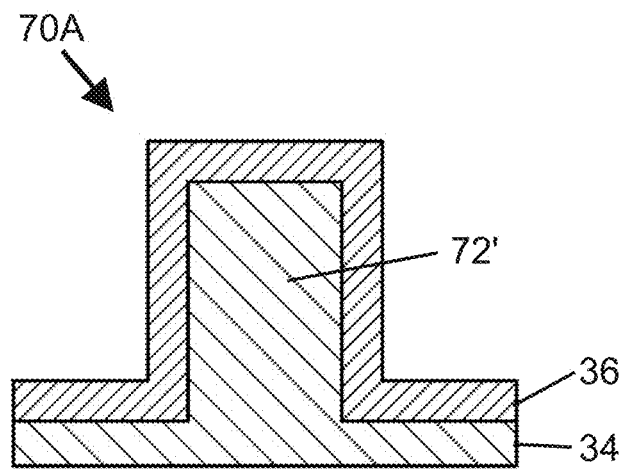
FIG. 8A is a magnified schematic cross-sectional view of a single protrusion (i.e., an anchoring feature) formed by an interface layer and an overlying self-assembled monolayer of a fluidic device, according to one embodiment.

FIG. 8A is a magnified schematic cross-sectional view of a single protrusion 70A (i.e., an anchoring feature) formed by an interface layer 34 and an overlying self-assembled monolayer (SAM) 36 of a fluidic device, according to one embodiment. The protrusion 70A includes an upwardly extending portion 72' of the interface layer 34, with the upwardly extending portion 72' being overlaid with the SAM 36. In certain embodiments, the interface layer 34 may be initially deposited with increased thickness, and regions of such material may be selectively removed (via any suitable subtractive material removal process) to form upwardly extending protrusions separated by troughs, whereby subtractive removal removes less than an entire thickness of the interface layer 34. In other embodiments, subtractive removal locally removes the entire thickness of the interface layer 34.

Figure 8B:
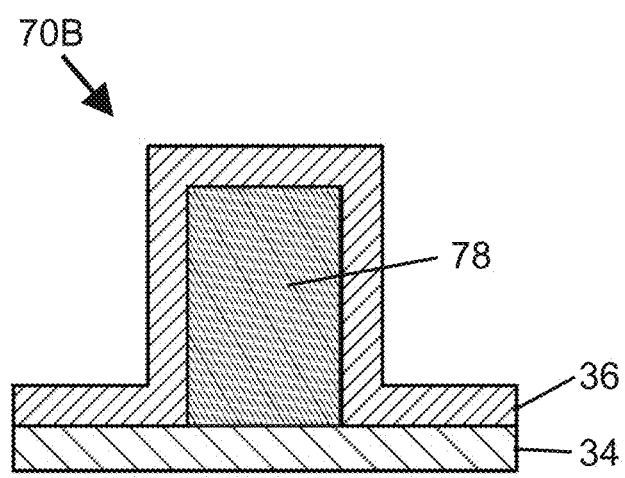
FIG. 8B is a magnified schematic cross-sectional view of a single protrusion (i.e., an anchoring feature) formed by a deposited material (e.g., photosensitive or photoimageable material) extending upward from a surface of an interface layer and being overlaid with a self-assembled monolayer, according to one embodiment.

FIG. 8B is a magnified schematic cross-sectional view of a single protrusion 70B (i.e., an anchoring feature) formed by a deposited material 78 (e.g., photosensitive or photoimageable material) extending upward from a surface of an interface layer 34 and being overlaid with a self-assembled monolayer (SAM) 36, according to one embodiment. Examples of materials that might be used for the deposited material 78 include, but are not limited to SU-8, photoresist, Parylene, epoxy, and polymers. In certain embodiments, a deposited material 78 may be applied over specified areas using an additive manufacturing process, and thereafter portions of the deposited material 78 may be removed using a subtractive process. In certain embodiments, the deposited material 78 comprises a photoimageable material to facilitate patterning.

Figure 9A:
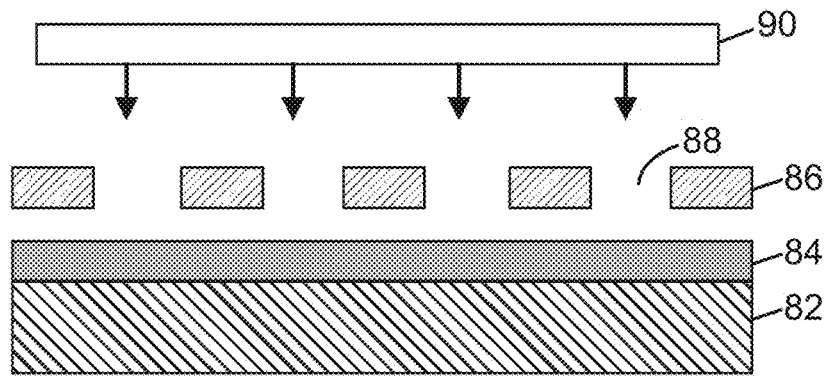
FIGS. 9A-9E provide schematic cross-sectional views of anchoring features producible by a subtractive process in various states of formation according to one embodiment.
Figure 9B:
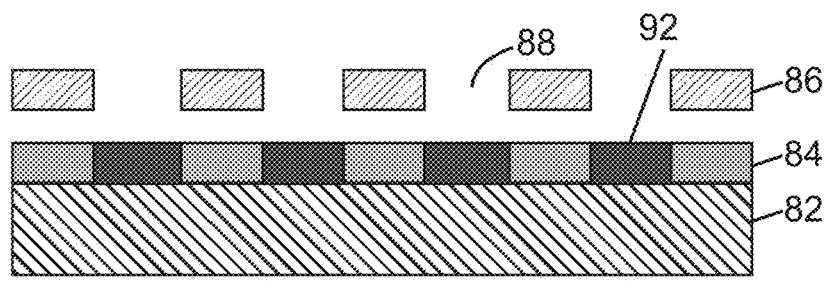
Figure 9C:
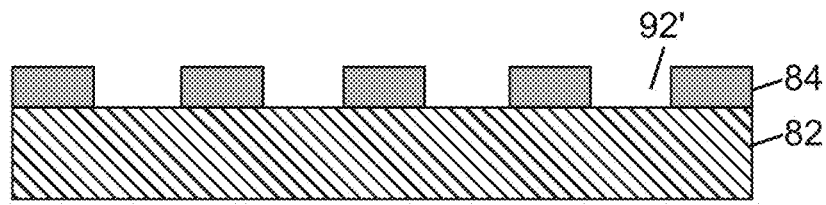
Figure 9D:
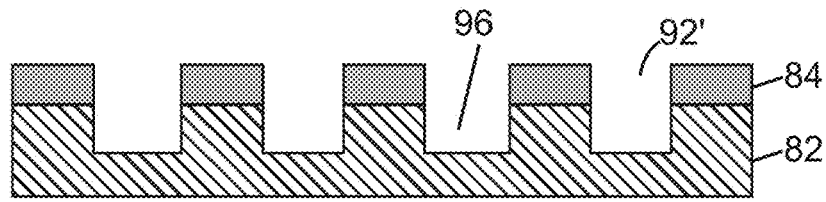
Figure 9E:
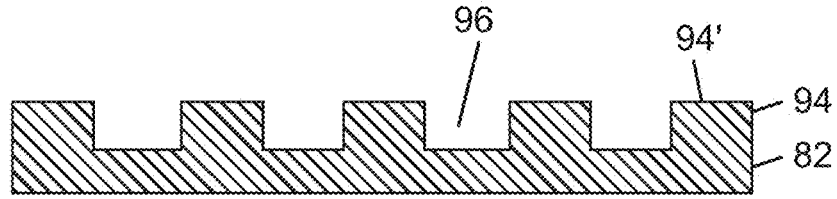

FIGS. 9A-9E provide schematic cross-sectional views of a portion of an interface layer 82 with recesses in various states of formation in an upper surface thereof using a process such as photolithographic patterning followed by selective etching to form anchoring features. FIG. 9A illustrates the interface layer 82 overlaid with a layer of photoresist 84, with a photomask 86 defining mask windows 88 arranged between the layer of photoresist 84 and an electromagnetic (e.g., ultraviolet) radiation source 90. FIG. 9B illustrates the photomask 86, interface layer 82, and layer of photororesist 84 following impingement of radiation through the mask windows 88 to form soluble regions 92 in the layer of photoresist 84. Such soluble regions 92 may be removed by application of a suitable developer chemical to yield a layer of photoresist 84 defining photoresist windows 92', as shown in FIG. 9C. Thereafter, a suitable etchant may be applied through the photoresist windows 92' to form grooves or recesses 96 in the interface layer 82, as shown in FIG. 9D. Finally, the layer of photoresist 84 may be removed to yield an interface layer 82 including an exposed upper surface 94' and grooves or recesses 96 that extend from the upper surface 94' into an interior of the interface layer 82, as shown in FIG. 9E. The resulting grooves or recesses 96 are separated by elevated regions or protrusions 94, with the foregoing elements being useable as anchoring features to promote adhesion of an overlying wall structure (not shown) bounding a fluidic passage of a fluidic device (e.g., a biosensor device). Although FIG. 9E shows the grooves or recesses 96 as extending through only a portion of a thickness of the interface layer 82, in certain embodiments, one or more grooves or recesses 96 may extend through the entire thickness of the interface layer 82.

Figure 10:
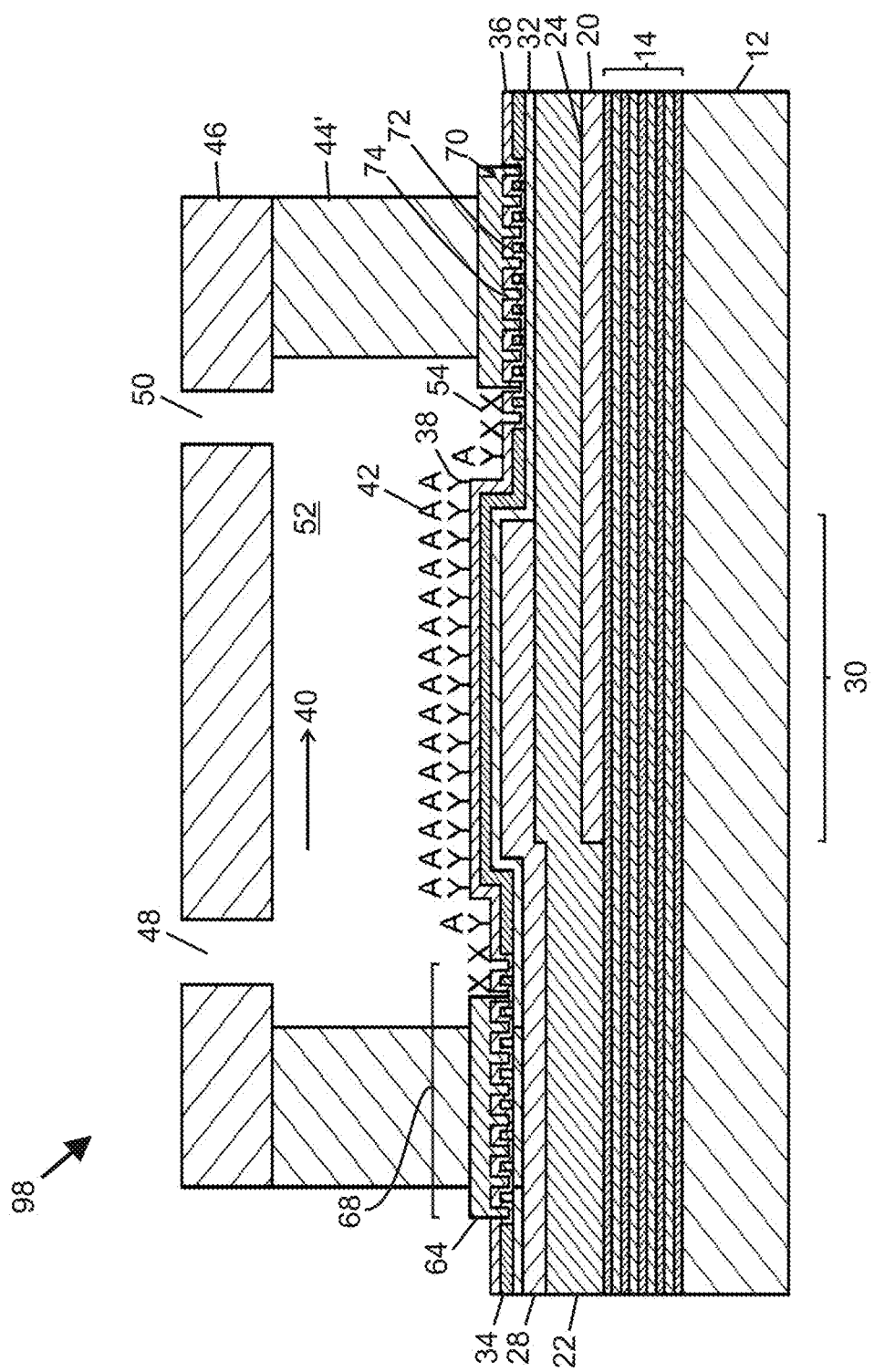
FIG. 10 is a schematic cross-sectional view of a portion of a fluidic device (e.g., a biochemical sensor device) including a fluidic passage bounded from below by a base structure including a BAW resonator structure, bounded from above by a cover or cap layer, and bounded laterally by a wall structure fabricated with photo-defined epoxy or resist materials, with the wall structure including a footer portion having a width that exceeds a width of an upper wall portion, and with the footer portion overlying anchoring regions including recesses and/or protrusions defined in or on the base structure, according to one embodiment.

FIG. 10 is a schematic cross-sectional view of a portion of a fluidic device 98 (e.g., a biochemical sensor device) including a fluidic passage 52 bounded from below by a base structure including a BAW resonator structure, bounded from above by a cover of cap layer 46, and bounded laterally by a wall structure fabricated with photo-defined epoxy or resist materials, with the wall structure including a footer portion 64 having a width that exceeds a width of an upper wall portion 44', and with the footer portion 64 overlying anchoring regions 68 including recesses 74 and/or protrusions 70 defined in or on the base structure, according to one embodiment. Use of a wall structure including a footer portion 64 (e.g., according to FIGS. 6A and 6B) and including anchoring regions 68 (e.g., according to FIG. 7) may provide further enhanced peeling resistance relative to use of one of these features alone.

Figure 11A:
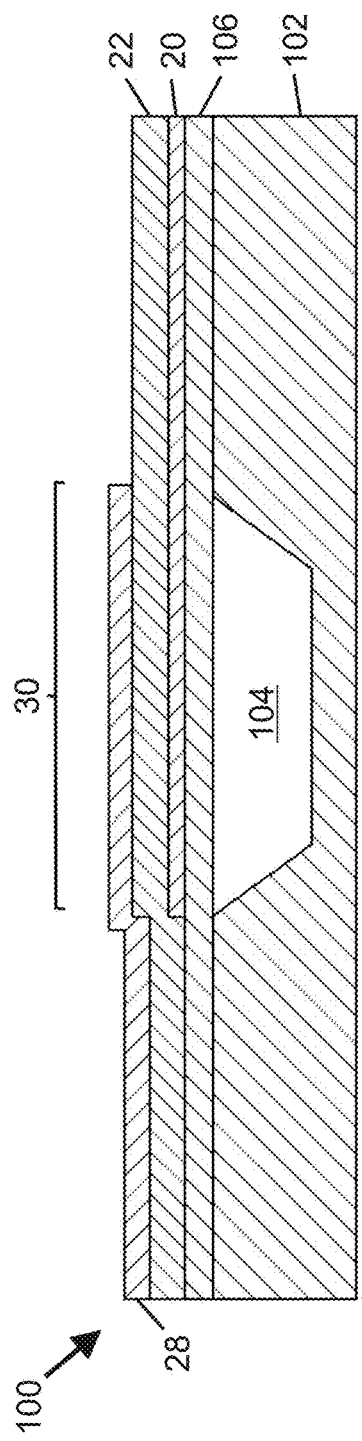
FIG. 11A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity optionally covered by a support layer, and an active region registered with the cavity, with a portion of the piezoelectric material arranged between overlapping portions of a top side electrode and a bottom side electrode.

The fluidic device 98 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the upper wall portion 44' are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Anchoring regions 68 include protrusions 70 and recesses 74, and are laterally displaced from (thereby being non-coincident with) the active region 30. Each protrusion 70 includes an upwardly extending segment 72 of an underlying layer (e.g., an interface layer 34) that is overlaid with the substantially continuous SAM 36. The footer portion 64 of the wall structure extends upward from the anchoring regions 68, and the upper wall portion 44' extends upward from the footer portion 64, to define lateral boundaries of the fluidic passage 52 containing the active region 30. The cover or cap layer 46 defines fluidic inlet and outlet ports 48, 50 (suitable for admitting a fluid volume 40 such as an analyte-containing sample) and is further provided to provide an upper boundary for the fluidic passage 52. Operation of the fluidic device 98 is substantially similar to the operation of the fluidic device 58 described in connection with FIG. 3. FIG. 11A is a schematic cross-sectional view of a film bulk acoustic wave resonator (FBAR) structure 100 including an active region 30, wherein at least portions of the active region 30 are subject to being overlaid with an interface layer and a self-assembled monolayer (SAM) suitable for receiving a functionalization (e.g., specific binding or non-specific binding) material, according to one embodiment. The FBAR structure 100 includes a substrate 102 (e.g., silicon or another semiconductor material) defining a cavity 104 optionally covered by a support layer 106 (e.g., silicon dioxide). A bottom side electrode 20 is arranged over a portion of the support layer 106, a piezoelectric material 22, preferably embodying inclined c-axis hexagonal crystal structure piezoelectric material (e.g., AlN or ZnO), is arranged over the bottom side electrode 20 and the support layer 106, and a top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 100. The active region 30 is arranged over and registered with the cavity 104 disposed below the support layer 106. The cavity 104 serves to confine acoustic waves induced in the active region 30 by preventing dissipation of acoustic energy into the substrate 102, since acoustic waves do not efficiently propagate across the cavity 104. In this respect, the cavity 104 provides an alternative to the acoustic reflector 14 illustrated in FIGS. 1, 3-4B, 6A, 7, and 10. Although the cavity 104 shown in FIG. 11A is bounded from below by a thinned portion of the substrate 102, in alternative embodiments at least a portion of the cavity 104 may extend through an entire thickness of the substrate 102. Steps for forming the FBAR structure 100 may include defining the cavity 104 in the substrate 102, filling the cavity 104 with a sacrificial material (not shown) optionally followed by planarization of the sacrificial material, depositing the support layer 106 over the substrate 102 and the sacrificial material, removing the sacrificial material (e.g., by flowing an etchant through vertical openings defined in the substrate 102 or the support layer 106, or lateral edges of the substrate 102), depositing the bottom side electrode 20 over the support layer 106, growing (e.g., via sputtering or other appropriate methods) the piezoelectric material 22, and depositing the top side electrode 28. In certain embodiments, the top side electrode 28, the piezoelectric material 22, and the bottom side electrode 20 in combination may be self-supporting, and the support layer 106 may be omitted and/or removed by etching in the vicinity of the active region 30.

Figure 11B:
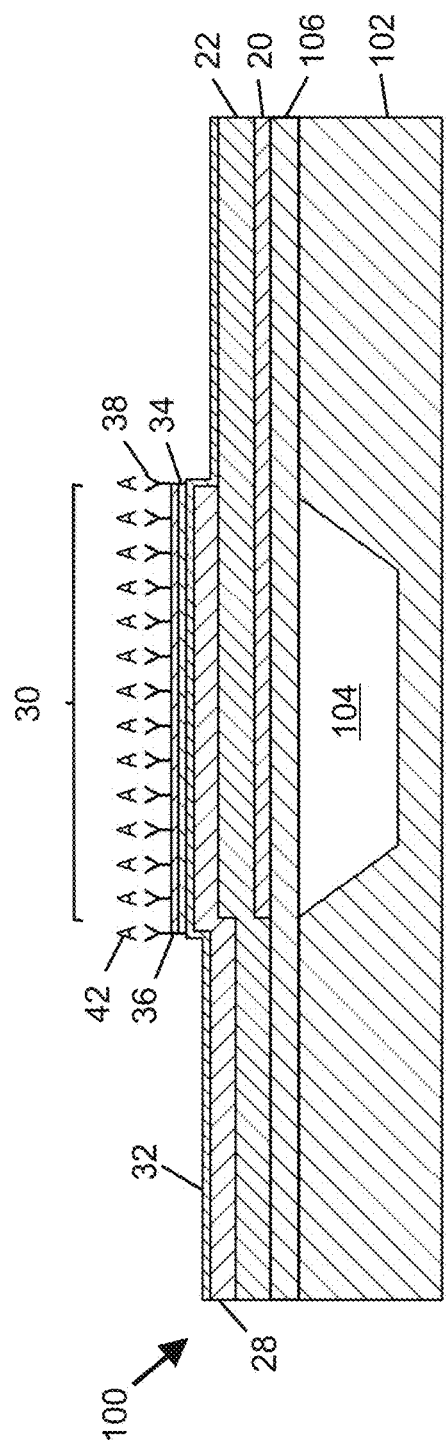
FIG. 11B is a schematic cross-sectional view of the FBAR structure according to FIG. 11A, following addition of a hermeticity layer, an interface layer, a self-assembled monolayer, and a functionalization (e.g., specific binding) material over at least portions of the FBAR structure.

FIG. 11B is a schematic cross-sectional view of the FBAR structure 100 according to FIG. 11A, following addition of a hermeticity layer 32, an interface layer 34, a self-assembled monolayer (SAM) 36, and functionalization material 38 (e.g., specific binding material). The hermeticity layer 32 is arranged over the entire piezoelectric material 22 (as well as the top side electrode 28), whereas the functionalization material 38, the SAM 36, and the interface layer 34 are arranged solely over the active region 30. As shown in FIG. 11B, analyte 42 is bound to the functionalization material 38, such as may occur following exposure of the functionalization material 38 to a medium (e.g., liquid or other fluid) containing the analyte 42, optionally as part of a microfluidic device.

As will be recognized by one skilled in the art upon review of the present disclosure, in certain embodiments, the FBAR structure 100 of FIGS. 11A and 11B may be substituted for the solidly mounted BAW resonator structures disclosed previously herein. In certain embodiments, the FBAR structure 100 of FIG. 11B may be incorporated in a fluidic device including composite wall structures (e.g., including a footer portion and an upper wall portion) and/or anchoring regions as disclosed herein, in order to promote persistent bonding between a wall structure and a base structure.

Figure 12:
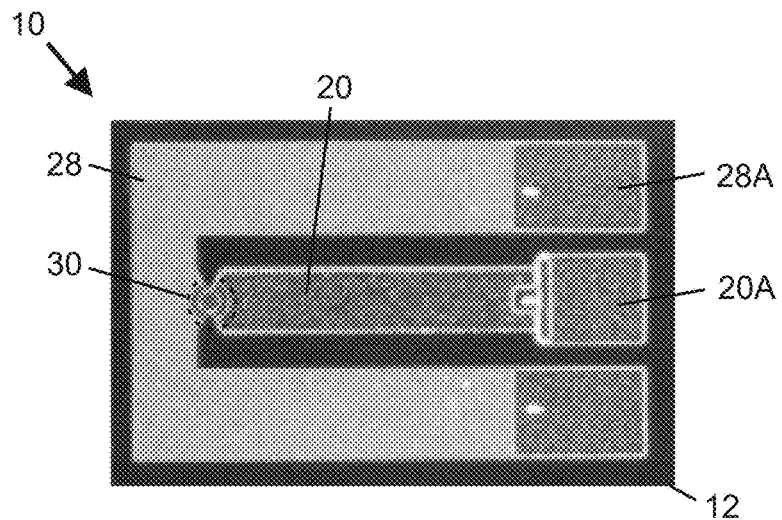
FIG. 12 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 12 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein, wherein the MEMS resonator device 10 may serve as a base structure of a fluidic device as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device, with wall structures fabricated of photosensitive materials such as SU-8. If desired, multiple resonator devices 10 may be provided in an array on a single substrate 12.

Figure 13:
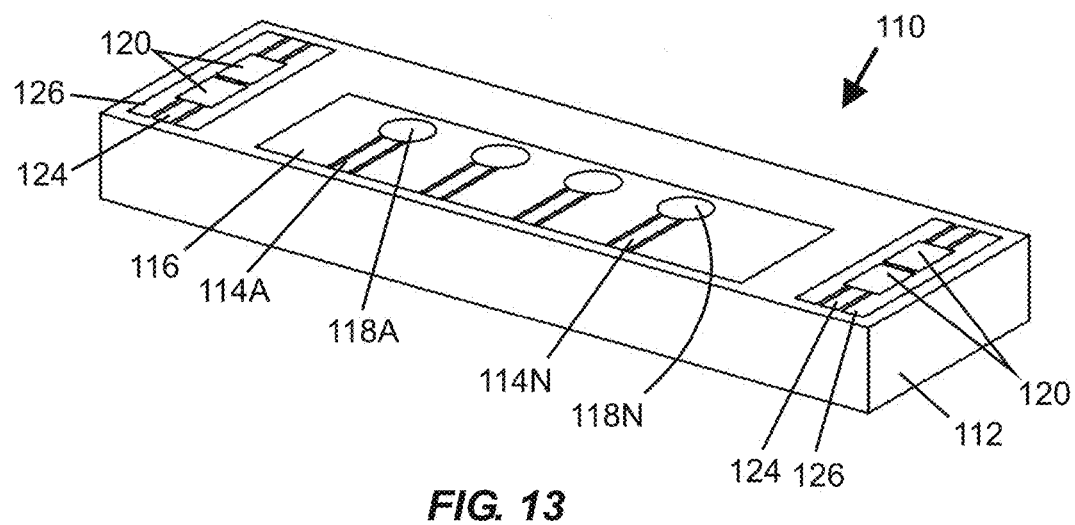
FIG. 13 is a perspective view of a base structure including multiple bulk acoustic wave MEMS resonator structures as disclosed herein, suitable for receiving a wall structure and a cover structure as disclosed herein in order to fabricate a multi-resonator fluidic device.

FIG. 13 is a perspective assembly view of a base structure 110 including multiple bulk acoustic wave MEMS resonator structures as disclosed herein, suitable for receiving a wall structure and a cover structure as disclosed herein in order to fabricate a multi-resonator fluidic device. The base structure 110 includes a substrate 112. Top central portions of the substrate 112, which includes an acoustic reflector (not shown) and a piezoelectric material (not shown), include a top side electrode 116 and bottom side electrodes 114A-114N. Regions in which the foregoing electrodes overlap one another and sandwich the piezoelectric material embody active regions 118A-118N. Any suitable number of active regions 118A-118N may be provided and fluidically arranged in series or parallel, although four active regions are illustrated in FIG. 13. Top peripheral (or top end) portions of the substrate 112 further include reference top side electrodes 126 and reference bottom side electrodes 124 in communication with reference overlap regions 120. Such reference overlap regions 120 are not intended to be exposed to fluid, and are present to provide a basis for comparing signals obtained from the active regions 118A-118N exposed to fluid when one or more fluidic channels are defined over the base structure 110.

Technical benefits obtainable with various embodiments of the present disclosure may include enhanced resistance of peeling and delamination of precisely dimensioned wall structures of fluidic devices incorporating bulk acoustic wave resonators, including devices suitable for biosensing or biochemical sensing applications.

Those skilled in the art will recognize improvements and modifications to the preferred embodiments of the present disclosure. All such improvements and modifications are considered within the scope of the concepts disclosed herein and the claims that follow.

What is claimed is:

1. A fluidic device comprising:
a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and
a wall structure arranged over at least a portion of the base structure and defining lateral boundaries of a fluidic passage arranged to receive a fluid and containing the active region;
wherein:
the wall structure comprises a footer portion and an upper wall portion that protrudes upward from the footer portion;
the footer portion is arranged between the upper wall portion and the base structure; and
the footer portion comprises a width that exceeds a width of the upper wall portion, wherein the wall structure comprises at least one of a photosensitive material, photoresist, or epoxy.

2. The fluidic device of claim 1, further comprising a cover structure arranged over the wall structure and defining an upper boundary of the fluidic passage.

3. The fluidic device of claim 2, wherein the wall structure and the cover structure are embodied in a monolithic body structure.

4. The fluidic device of claim 1, further comprising at least one functionalization material arranged over at least a portion of the active region.

5. The fluidic device of claim 4, further comprising a self-assembled monolayer arranged between the at least one functionalization material and the top side electrode.

6. The fluidic device of claim 5, further comprising an interface layer arranged between the self-assembled monolayer and the top side electrode.

7. The fluidic device of claim 6, further comprising a hermeticity layer arranged between the interface layer and the top side electrode.

8. A method for biological or chemical sensing, the method comprising:
supplying a fluid containing an analyte into the fluidic passage of the fluidic device according to claim 4, wherein said supplying is configured to cause at least some of the analyte to bind to the at least one functionalization material;
inducing a bulk acoustic wave in the active region; and
sensing a change in at least one of an amplitude-magnitude property, a frequency property, or a phase property of the at least one bulk acoustic wave resonator structure to indicate at least one of presence or quantity of target species bound to the at least one functionalization material.

9. The fluidic device of claim 1, wherein the piezoelectric material comprises a c-axis having an orientation distribution that is predominantly non-parallel to normal of a face of the substrate.

10. The fluidic device of claim 1, wherein a portion of the base structure comprises at least one anchoring region having at least one anchoring feature comprising at least one of: (i) at least one recess or (ii) at least one protrusion, and wherein the footer portion overlies the anchoring region.

11. The fluidic device of claim 10, wherein the at least one anchoring feature comprises a vertical dimension of least about 1 micron.

12. The fluidic device of claim 10, wherein the at least anchoring features comprises a plurality of recesses and a plurality of protrusions.

13. A fluidic device comprising:
a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, a bottom side electrode arranged below at least a portion of the piezoelectric material, wherein a portion of the piezoelectric material is arranged between the top side electrode and the bottom side electrode to form an active region, at least one functionalization material arranged over at least a portion of the active region; a self-assembled monolayer arranged between the at least one functionalization material and the top side electrode; an interface layer arranged between the self-assembled monolayer and the top side electrode; a hermeticity layer arranged between the interface layer and the top side electrode; and
a wall structure arranged over at least a portion of the base structure and defining lateral boundaries of a fluidic passage arranged to receive a fluid and containing the active region;
wherein:
the wall structure comprises a footer portion and an upper wall portion that protrudes upward from the footer portion;
the footer portion is arranged between the upper wall portion and the base structure; and
the footer portion comprises a width that exceeds a width of the upper wall portion.

14. The fluidic device of claim 13, further comprising a cover structure arranged over the wall structure and defining an upper boundary of the fluidic passage.

15. The fluidic device of claim 14, wherein the wall structure and the cover structure are embodied in a monolithic body structure.

16. The fluidic device of claim 14, wherein the cover structure defines an inlet port to the fluidic passage and outlet port from the fluidic passage.

17. The fluidic device of claim 13, wherein the piezoelectric material comprises a c-axis having an orientation distribution that is predominantly non-parallel to normal of a face of the substrate.

18. The fluidic device of claim 13, wherein a portion of the base structure comprises at least one anchoring region having at least one anchoring feature comprising at least one of: (i) at least one recess or (ii) at least one protrusion, and wherein the footer portion overlies the anchoring region.

19. The fluidic device of claim 18, wherein the at least one anchoring feature comprises a vertical dimension of least about 1 micron.

20. The fluidic device of claim 18, wherein the at least anchoring features comprises a plurality of recesses and a plurality of protrusions.

21. A fluidic device comprising:
a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, a bottom side electrode arranged below at least a portion of the piezoelectric material, wherein a portion of the piezoelectric material is arranged between the top side electrode and the bottom side electrode to form an active region, a self-assembled monolayer arranged over at least a portion of the active region; an interface layer arranged between the self-assembled monolayer and the top side electrode; a hermeticity layer arranged between the interface layer and the top side electrode; and
a wall structure arranged over at least a portion of the base structure and defining lateral boundaries of a fluidic passage arranged to receive a fluid and containing the active region;
wherein:
the wall structure comprises a footer portion and an upper wall portion that protrudes upward from the footer portion;
the footer portion is arranged between the upper wall portion and the base structure; and
the footer portion comprises a width that exceeds a width of the upper wall portion.

\* \* \* \* \*